United States Patent [19]

Nonami et al.

[11] Patent Number: 5,082,808

[45] Date of Patent: * Jan. 21, 1992

[54] CERAMIC MATERIAL AND METHOD FOR MAKING

[75] Inventors: Tohru Nonami, Ichikawa; Nobuo Yasui, Narita, both of Japan

[73] Assignee: TDK Corporation, Tokyo, Japan

[ * ] Notice: The portion of the term of this patent subsequent to Jul. 16, 2008 has been disclaimed.

[21] Appl. No.: 593,299

[22] Filed: Oct. 4, 1990

Related U.S. Application Data

[63] Continuation of Ser. No. 441,775, Dec. 27, 1989, abandoned, which is a continuation of Ser. No. 374,989, Jul. 3, 1989.

[30] Foreign Application Priority Data

| | | | |
|---|---|---|---|
| Jul. 4, 1988 | [JP] | Japan | 63-164959 |
| Jul. 4, 1988 | [JP] | Japan | 63-164960 |
| Aug. 26, 1988 | [JP] | Japan | 63-210669 |
| Oct. 26, 1988 | [JP] | Japan | 63-268102 |
| Jan. 12, 1989 | [JP] | Japan | 1-5388 |
| Feb. 16, 1989 | [JP] | Japan | 1-34967 |
| Aug. 10, 1989 | [JP] | Japan | 1-205781 |

[51] Int. Cl.$^5$ .............. C04B 35/02; C04B 35/10; C04B 35/56; C04B 35/58
[52] U.S. Cl. .............. 501/95; 501/1; 106/35
[58] Field of Search .............. 501/1, 95; 106/35

[56] References Cited

U.S. PATENT DOCUMENTS

| | | | |
|---|---|---|---|
| 4,230,455 | 10/1980 | Hidata et al. | 433/202 |
| 4,503,157 | 3/1985 | Hatahira | 501/1 |
| 4,772,573 | 9/1988 | Toriyama et al. | 501/1 |

FOREIGN PATENT DOCUMENTS

| | | |
|---|---|---|
| 0275652 | 7/1988 | European Pat. Off. . |
| 0353476 | 2/1990 | European Pat. Off. . |

OTHER PUBLICATIONS

WPIL File Supplier Accession No. 88-327454 [46] JP 63242263 Abstract.

*Primary Examiner*—Mark L. Bell
*Assistant Examiner*—Deborah Jones
*Attorney, Agent, or Firm*—Oblon, Spivak, McClelland, Maier & Neustadt

[57] ABSTRACT

A ceramic material for use as artificial bone and dental root is provided which takes the form of a composite sintered body comprising crystalline calcium phosphate grains as a matrix and inorganic whiskers dispersed therein. An intermediate layer containing elements in either one or both of the whiskers and the grains intervenes between the whiskers and the grains. The material has physical toughness and strength as well as biomedical affinity. The material is prepared by mixing calcium phosphate and a whisker-forming material or whiskers and sintering the mixture at a temperature of 800° to 1600° C., followed by slow cooling to allow formation of the intermediate layer.

16 Claims, 4 Drawing Sheets

CERAMIC MATERIAL AND METHOD FOR MAKING

This application is a continuation of application Ser. No. 07/441,775, filed on Nov. 27, 1989, now abandoned, which is a continuation of application Ser. No. 07/374,989, filed July 3, 1989, which is pending.

This invention relates to a ceramic material in the form of a whisker-reinforced sintered body and a method for making the same. More particularly, it relates to a ceramic material for use as artificial bone and dental root in the form of a sintered body based on calcium phosphate having biological affinity and reinforced with whiskers as well as a method for making the same.

BACKGROUND OF THE INVENTION

Calcium phosphate materials including hydroxyapatite and tricalcium phosphate are widely used as living hard tissue replacements such as artificial bones and dental roots because their sintered bodies are non-toxic and likely to bond with the bone in a living system. Sintered calcium phosphate, however, is not necessarily satisfactory in practice because it is neither mechanically strong nor tough. Sintered calcium phosphate tends to break or chip away when it is shaped to a configuration conforming to a deficient site in a living system, implanted and embedded in the site.

Japanese Patent Application Kokai No. 57971/1984 discloses fibrous or acicular apatite which is reinforced with mineral fibers. This composition, however, is impractical in that manufacture of apatite in fiber or needle form is very difficult and mineral fibers having affinity thereto must be separately prepared. It is a cumbersome operation to sinter apatite in close contact with mineral fibers under pressure at a relatively low temperature of lower than 800° C. under conditions to prevent substantial escape of moisture. In addition, such low temperature sintering results in a low relative density. Many problems must be overcome before this composition can be used in practice.

Japanese Patent Application Kokai No. 162676/1987 discloses a composite apatite material of whisker reinforcement type in which mullite whiskers are simultaneously grown during sintering of apatite. Simple precipitation of mullite whiskers, however, will result in a sintered body which is not strong or tough enough to prevent chipping and cracking upon implantation, that is, application to a deficient site in a living system.

Also, whisker-reinforced sintered bodies are known from Japanese Patent Application Kokai No. 151652/1988 disclosing a sintered body which is reinforced with SiC whiskers using a hot isostatic press (HIP) technique and Japanese Patent Application Kokai No. 27308/1988 disclosing the use of various mineral whiskers. In the former, sintering is carried out in the presence of sintering aids, but to an unsatisfactory degree of reinforcement because no measure is taken such that the sintering aids may control the interface between the whiskers and the matrix. In the latter, the mixture must be sintered at relatively low temperatures so that the whiskers and the matrix may not react with each other because it is difficult to properly control the interface between the whiskers and the matrix. Then no satisfactory reinforcement can be achieved.

It is thus desired to eliminate the drawbacks of prior art whisker-reinforced calcium phosphate sintered bodies.

SUMMARY OF THE INVENTION

An object of the present invention is to provide a novel and improved ceramic material in the form of a sintered body of the whisker reinforcement type having high strength and increased toughness.

Another object of the present invention is to provide a method for making such a ceramic material.

Making efforts in search of a sintered body of the whisker reinforcement type having high strength and toughness, the inventors have found that the object is achieved with crystalline calcium phosphate grains having whiskers dispersed therebetween when an intermediate layer containing an element or elements in the whiskers and/or the grains intervenes between the whiskers and the grains.

According to the present invention, there is provided a ceramic material in the form of a composite sintered body comprising crystalline calcium phosphate grains as a matrix and inorganic whiskers dispersed therein wherein an intermediate layer containing elements in either one or both of the whiskers and the grains is present between the whiskers and the grains.

Preferably, the intermediate layer has a continuous or stepwise gradient of concentration. More preferably, the gradient of concentration of elements in the whiskers is opposite to the gradient of concentration of elements in the grains.

Preferably, the crystalline calcium phosphate is of apatite series. Most often, it is a hydroxyapatite having an atomic calcium-to-phosphorus (Ca/P) ratio of from 165/100 to 175/100.

Preferably, the inorganic whiskers are selected from the group consisting of silicon carbide, boron carbide, silicon nitride, carbon, alumina, zirconia, calcium silicate, aluminum silicate, aluminum silicate calcium, calcium silicate magnesium, calcium aluminate, magnesium silicate, and metal whiskers. Most often, the inorganic whiskers contain at least one inorganic oxide selected from the group consisting of calcium oxide, silicon oxide, aluminum oxide, and magnesium oxide.

Preferably, the whiskers occupy 0.5 to 95% by area of a cross section of the sintered body.

A ceramic material as defined may be prepared by the steps of mixing a calcium phosphate material and an inorganic whisker-forming material, sintering the mixture at a sufficient temperature of 800 to 1600° C for a sufficient time to allow whiskers to grow, and cooling the mixture from the sintering temperature at a sufficiently slow rate to allow a desired intermediate layer to form between the matrix grains and the whiskers.

Also, the ceramic material may be prepared by the steps of mixing a calcium phosphate material and inorganic whiskers, sintering the mixture at a temperature of 800 to 1600° C., and cooling the mixture from the sintering temperature at a sufficiently slow rate to allow a desired intermediate layer to form between the matrix grains and the whiskers.

Further, the ceramic material may be prepared by the steps of mixing a calcium phosphate material and inorganic whiskers, and an intermediate layer-forming material, sintering the mixture at a temperature of 800 to 1600° C., and cooling the mixture from the sintering temperature at a sufficiently slow rate to allow a desired intermediate layer to form between the matrix grains and the whiskers.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE INVENTION

Figure 1:
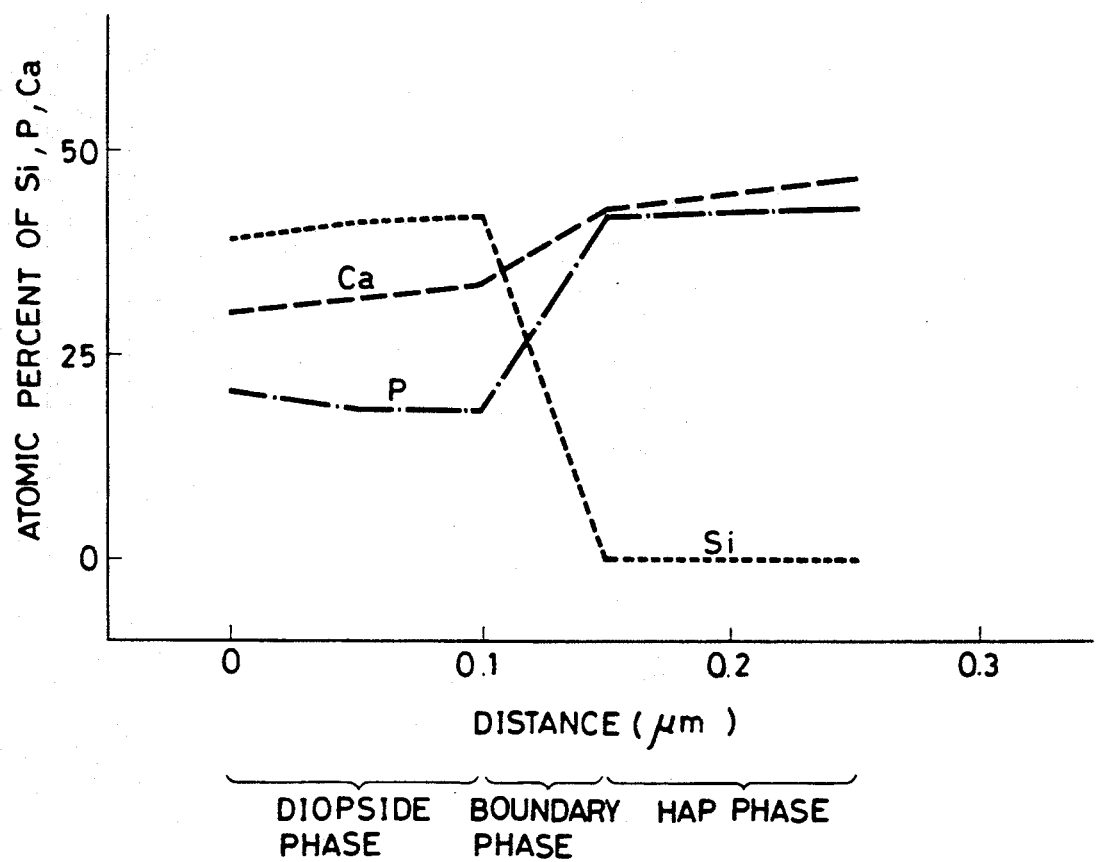
FIG. 1 is a diagram showing a change of the composition across an intermediate layer in ceramic material sample No. 4 in Example 1.

The ceramic material of the present invention is in the form of a composite sintered body comprising crystalline calcium phosphate grains as a matrix and inorganic whiskers dispersed therein. An intermediate layer containing elements in either one or both of the whiskers and the grains intervenes between the whiskers and the grains. Preferably, the intermediate layer has a continuous or stepwise gradient of concentration of the elements.

The intermediate layer may generally have a thickness of up to 3 μm, preferably from 0.005 to 3 μm, more preferably from 0.01 to 1.0 μm. Too thinner intermediate layers fail to provide sufficient bond strength and are difficult to form whereas too thicker layers adversely affect strength and tend to change or degrade the hydroxyapatite and whisker components because of excessive reaction.

The crystalline calcium phosphate grains as the matrix may generally have a grain size of 0.05 to 30 μm, preferably 0.1 to 20 μm, more preferably 0.1 to 10 μm. A grain size smaller than the lower limit is difficult to manufacture whereas a grain size larger than the upper limit results in a reduced strength.

The inorganic whiskers are selected from the group consisting of silicon carbide whiskers, boron carbide whiskers, silicon nitride whiskers, carbon whiskers, alumina whiskers, zirconia whiskers, calcium silicate whiskers, aluminum silicate whiskers, aluminum silicate calcium whiskers, calcium silicate magnesium whiskers, calcium aluminate whiskers, magnesium silicate whiskers, and metal whiskers (such as titanium whiskers and titanium alloy whiskers).

Whiskers containing at least one inorganic oxide selected from the group consisting of calcium oxide, silicon oxide, aluminum oxide, and magnesium oxide are preferred for biological affinity or compatibility. Included are alumina whiskers, zirconia whiskers, aluminum silicate calcium whiskers such as anorthite ($CaO \cdot 2SiO_2 \cdot Al_2O_3$) whiskers, calcium silicate magnesium whiskers such as diopside ($CaO \cdot 2SiO_2 \cdot MgO$) whiskers, and calcium silicate whiskers such as wollastonite ($CaO \cdot SiO_2$) whiskers. Among them, diopside whiskers, anorthite whiskers and wollastonite whiskers, especially diopside whiskers are most preferred. The whiskers may have a composition deviating more or less from their stoichiometry shown above.

The whiskers each have a length and a diameter. The whisker length is generally in the range of from 0.05 to 2,000 μm, preferably from 0.05 to 100 μm, more preferably from 0.2 to 30 μm, most preferably from 0.2 to 15 μm. The whisker diameter is generally in the range of from 0.05 to 100 μm, preferably from 0.05 to 5 μm. The aspect ratio defined as length divided by diameter is in the range of from 1.2/1 to 100/1, preferably 1.2/1 to 50/1, more preferably from 2/1 to 20/1, most preferably from 5/1 to 15/1. Shorter whiskers outside the length range would be less effective whereas longer whiskers tend to induce strain. Whiskers having an aspect ratio of less than 1 are least effective whereas whiskers having an aspect ratio of more than 100 tend to induce strain.

The ratio of matrix grain size to whisker length is in the range of from 10/1 to 1/10, preferably from 5/1 to 1/10, more preferably from 14/10 to 2/10, most preferably from 1/1 to 2/10. With smaller ratios, the whiskers do not fully exert their function of increasing strength whereas with smaller ratios, strains are induced upon sintering, losing strength.

The whiskers occupy 0.5 to 95% by area, preferably 1 to 70% by area, more preferably 5 to 60% by area, most preferably 5 to 40% by area of a cross section of the sintered body. Outside the range, sintered bodies having less amounts of whiskers are less tough whereas sintered bodies having excess amounts of whiskers are low in biological affinity. The percent area that whiskers occupy in a cross section of the sintered body can be determined using a photomicrograph. More particularly, a sintered body sample is sectioned. The section is mirror polished, and then chemically etched with aqueous 1-5% HCl or thermally etched at a temperature of higher than 800° C., but lower than the whisker forming temperature. The section is then observed under a scanning electron microscope. The photo micrograph is then transferred to a section paper, from which the percent area of whiskers is calculated by counting the corresponding sections. The procedure may be repeated five times, for example, determining the percent area of whiskers. If the whiskers show biomedical affinity, for example, calcium silicate, calcium magnesium silicate, calcium aluminum silicate or other similar whiskers, the whisker content can be increased to 99% by area.

In the practice of the present invention, the composite sintered body can be manufactured by either a precipitation method or a mixing method. The precipitation method is by mixing an inorganic whisker-forming material with a matrix-forming calcium phosphate compound and sintering the mixture thereby causing whiskers to grow or precipitate. The mixing method involves mixing pre-formed whiskers with a matrix-forming calcium phosphate compound and sintering the mixture. The mixing method has an advantage of an increased freedom of choice of feasible whiskers although the precipitation method is more advantageous with respect to whiskers-to-matrix adherence, strength, toughness, and biological affinity.

The calcium phosphate materials used as sintering stock material in the practice of the present invention include a variety of calcium phosphate compounds, for example, tri-calcium phosphate $Ca_3(PO_4)_2$, and apatite series calcium phosphates such as hydroxyapatite and fluoroapatite. They may be used alone or in admixture of two or more. Preferred calcium phosphates are of the apatite series. These apatites may be either synthetic apatites prepared by dry and wet processes or biotic apatites collected from bones and teeth of various vertebrate animals. A typical dry synthetic process is by reacting calcium phosphate with excess CaO in a steam stream at a high temperature of 900 to 1300° C.

The preferred calcium phosphate materials used herein are apatites, especially hydroxyapatites, having an atomic calcium to phosphorus (Ca/P) ratio between 165/100 and 175/100. If the Ca/P atom ratio is less than 165/100, there is some likelihood that part of whiskers, whisker-forming material or an intermediate layer forming component to be described later would form a solid solution with the hydroxyapatite, inducing a change in the composition of whiskers. As a result, whiskers might not fully precipitate. Further, partial formation of tricalcium phosphate would induce strains and lose strength and biological affinity.

The calcium phosphate materials are generally used in power form having a size of about 0.1 to 1,000 μm or granular form having a size of about 0.1 to 3 mm.

In preparing the composite sintered body of the invention by the precipitation method, the whisker-forming material is generally used in an amount of about 0.5 to about 95% by weight, preferably about 1 to about 70% by weight, more preferably about 5 to about 60% by weight, most preferably about 5 to 40% by weight based on the total weight of sintering stock material, that is, calcium phosphate material plus whisker-forming material. In general, the whisker-forming material is added to and mixed with the calcium phosphate material in the above-defined proportion, and the mixture is sintered at a temperature of 800 to 1,600° C. Then there is obtained a composite sintered body having a whisker content of 0.5 to 90% by area.

The whisker-forming materials, that is, materials which can convert into whiskers under sintering conditions include, for example, silicon oxide, calcium oxide, magnesium oxide, and aluminum oxide, as well as those which can convert into these compounds upon sintering, such as corresponding carbonates, bicarbonates, and hydroxides. These materials may be used in the form of powder, granules, slurry, and aqueous solution.

These whisker-forming materials may be blended in such a proportion corresponding to the composition of the desired whiskers. Useful are a blend comprising a silica source in an amount of 0.05 to 600 parts by weight of $SiO_2$ and a calcium oxide source in an amount of 0.05 to 600 parts by weight of CaO or an alumina source in an amount of 0.05 to 600 parts by weight of $Al_2O_3$; and a blend comprising a silica source in an amount of 0.05 to 800 parts by weight of $SiO_2$, a calcium oxide source in an amount of 0.05 to 600 parts by weight of CaO, and at least one of an alumina source in an amount of 0.05 to 600 parts by weight of $Al_2O_3$ and a magnesia source in an amount of 0.05 to 600 parts by weight of MgO, all parts being per 100 parts by weight of the calcium phosphate material. In the latter case, the sources may be blended in such proportions that 1 to 4 mol of silica, 0.5 to 3 mol of alumina and 0.5 to 3 mol of magnesia are present per mol of calcium oxide. In addition, one or more of zirconia, strontium oxide, and barium oxide sources may be used in sufficient amounts to provide up to 20 parts by weight of $ZrO_2$, SrO, and BaO on the same basis as above. When it is desired to grow diopside whiskers, for example, the sources may be blended in such proportions that 0.05 to 14 mol, preferably 0.5 to 5 mol, more preferably 0.8 to 2.5 mol of magnesium oxide and 0.05 to 10 mol, preferably 2 to 5 mol, more preferably 2 to 3 mol of silica are present per mol of calcium oxide. When it is desired to grow anorthite whiskers, for example, the sources may be blended in such proportions that 0.1 to 20 mol, preferably 0.2 to 1.5 mol, more preferably 0.8 to 1.2 mol of alumina and 1 to 10 mol, preferably 2 to 5 mol, more preferably 2 to 3 mol, most preferably 2 to 2.5 mol of silica are present per mol of calcium oxide. These components may also be used in powder or granule form like the calcium phosphate component.

A mixture of two types of stock materials, a calcium phosphate-forming component and a whisker-forming component as described above, is sintered into a composite sintered body consisting essentially of crystalline calcium phosphate and whiskers (typically, diopside or anorthite). The presence of matrix and whisker by-products created upon sintering is permitted as long as the desired effect is not impaired. In the examples mentioned above, permissible is inclusion of such by-products as α-tricalcium phosphate and other oxides such as forsterite and wollastonite in the case of diopside whiskers. The by-products are usually copresent in the matrix.

In the composite sintered body, the calcium phosphate forming the matrix is present as grains (or crystals) and the whiskers are dispersed in the matrix.

The composite sintered body of the invention may also be prepared by the mixing method involving using pre-formed whiskers rather than the whisker-forming material used in the precipitation method, mixing the pre-formed whiskers U with the calcium phosphate material, and sintering the mixture at a temperature of 800 to 1,600° C. The pre-formed whiskers may be selected from the previously listed ones. Whiskers containing at least one inorganic oxide selected from the group consisting of calcium oxide, silicon oxide, aluminum oxide, and magnesium oxide are preferred for biological affinity or compatibility. Anorthite and diopside whiskers are most preferred. The pre-formed whiskers may have dimensions equivalent to the whiskers in the ceramic material. The pre-formed whiskers may generally be used in an amount of about 0.5 to 95% by weight, preferably about 1 to 70% by weight, more preferably about 5 to 60% by weight, most preferably about 5 to 40% by weight based on the total weight of the sintering stock material mixture (calcium phosphate material plus whiskers).

The sintered body is then slowly cooled down from the sintering temperature, obtaining a desired ceramic material. Cooling may preferably be carried out at a rate of about 0.2 to 30° C. min., more preferably about 0.5 to 10° C./min.

It is also possible to form the ceramic material of the invention by mixing a calcium phosphate material, pre-formed whiskers, and an intermediate layer-forming material, sintering the mixture, and cooling the sintered body at a sufficiently slow rate to allow a desired intermediate layer to form. Sintering and cooling may be carried out under the same conditions as previously described.

The intermediate layer-forming material contains at least one member of the components of the matrix and whisker materials. The components of the matrix material include calcium oxide and phosphorus oxide, for example. The components of the whisker material vary with a particular type of whisker and include calcium oxide, silicon oxide, magnesium oxide or the like in the case of diopside whiskers, and calcium oxide, silicon oxide, aluminum oxide or the like in the case of anorthite whiskers. These components may also be those materials which can convert into the aforementioned ones under sintering conditions, for example, carbonates, bicarbonates, and hydroxides of corresponding elements. The intermediate layer-forming material may be used in an amount of from about 0.05 to 5% by weight, preferably from about 0.5 to 2% by weight based on the total weight of the sintering stock material. Larger amounts would form an intermediate layer of an increased thickness, lowering strength.

The preparation of a ceramic material according to one embodiment of the present invention will be illustrated. Most often, the starting material is powder calcium phosphate material. A predetermined amount of whiskers or whisker-forming materials in powder form is added to the powder calcium phosphate material along with a dispersant. The whisker-forming materials are materials that can transform into whiskers under sintering conditions, for example, silica, calcium oxide, magnesium oxide, and alumina, and may be added separately or as a premix. Use of sources which produce materials that can together form whiskers under sintering conditions is also contemplated. Materials having whisker compositions such as the anorthite and diopside compositions are also useful. The pre-formed whiskers, e.g., diopside or anorthite whiskers may also be used along with the intermediate layer-forming material.

The dispersant assists in uniformly dispersing whiskers or whisker-forming materials in powder calcium phosphate material. Examples of the dispersant include anionic surface-active agents such as carboxylate salts and sulfonate salts.

The thus prepared powder mixture is shaped into a desired shape by a conventional method such as press molding and slip casting, dried, and then sintered in air at a temperature of 800 to 1,600° C., preferably 1,000 to 1,400° C., more preferably 1,100 to 1,300° C. The sintering time is generally in the range of from about 5 minutes to about 5 hours.

The sintered body is then slowly cooled down from the sintering temperature, preferably at a slow constant rate of about 0.2 to 30° C./min., more preferably about 0.5 to 10° C./min., obtaining a desired ceramic material having an intermediate layer between grains and whiskers.

Sintering creates a crystalline calcium phosphate matrix or crystalline calcium phosphate matrix and whiskers at the same time when the whisker-forming material is used. There is obtained a composite sintered body in which whiskers are dispersed in the crystalline calcium phosphate matrix, both the matrix and whiskers meeting the dimensional requirements, and the intermediate layer is interposed between the grains and the whiskers, preferably around most of the boundary, most preferably around the entire boundary.

Provision of an intermediate layer between whiskers and grains prevents direct reaction between whiskers and grains so that the whiskers change no longer maintaining sufficient strength, improves the bond between whiskers and grains also contributing to strength, and enables easy control of the interface between whiskers and grains. As a result, the sintered body is reinforced more densely, further improving mechanical strengths such as flexural strength and toughness. Particularly when the intermediate layer has a continuous or stepwise gradient of concentration of elements, the bond between whiskers and grains is further improved. The concentration of an element or elements of the whiskers has an opposite gradient to the concentration of an element or elements of the grains in a direction between each whisker and the adjoining grain.

The ceramic materials of the invention maintain the desirable properties of calcium phosphate material, for example, biological affinity of apatite as artificial bone. The ceramic materials have so high strength and toughness that they may be widely utilized as artificial bone, dental root and joint materials for treatments in orthopedic surgery, dental and oral surgery.

The present method can readily impart high strength and toughness to a ceramic material of calcium phosphate grain matrix and whiskers by forming an intermediate layer between the whiskers and the grains.

EXAMPLE

Examples of the present invention are given below by way of illustration and not by way of limitation.

Relative density (porosity), flexural strength, toughness, whisker content, and intermediate layer thickness were measured by following procedures.

RELATIVE DENSITY (POROSITY)

The density of a sintered sample was measured by the Archimedian method. The sintered sample was pulverized into powder having a surface area of 5 $m^2/g$ which was measured for true density. Relative density (%) was calculated from the apparent and true densities.

FLEXURAL STRENGTH

Ten test specimens of $3 \times 4 \times 40$ mm were cut out and mirror polished. They were measured by the three point bending test with a span of 36 mm and a cross head speed of 0.5 mm/min.

TOUGHNESS

Three test specimens of $3 \times 4 \times 40$ mm were cut out, mirror polished, and formed with a notch of 1.5 mm deep at the center. They were measured for fracture toughness ($K_{IC}$) by the three point bending test with a span of 36 mm and a cross head speed of 0.5 mm/min.

(4) Whisker content, % by area

A section of a sample was mirror polished, thermally etched at 800–1200° C., and observed under a scanning electron microscope (SEM) to measure the proportion (%) of whiskers in the sectional area. The whisker content (%) is an average of five measurements.

(5) Intermediate layer thickness

The thickness of a grain boundary was measured from a photomicrograph taken under a transmission electron microscope (TEM).

The amounts of respective materials are expressed in % by weight based on the total weight of a sintering stock material, that is, a mixture of the respective materials.

EXAMPLE 1

As reported in Table 1, hydroxyapatite (HAP) and whisker-forming material were milled along with a dispersant in a ball mill for one hour. The slurry was filtered through a qualitative filter paper. The collected cake was dried at 120° C. for 5 hours and a 50-gram portion of the cake was then molded in a mold of 40 mm by 50 mm under a pressure of 300 kg/cm$^2$. The molded material was sintered at the temperature shown in Table 1 for 2 hours. The resulting sintered body was slowly cooled down from the sintering temperature at the rate shown in Table 1, obtaining a ceramic material.

The hydroxyapatites used had an atomic calcium-to-phosphorus (Ca/P) ratio of 1.67 and the BET values shown in Table 1.

The whisker-forming materials used were anorthite and diopside as identified below. The amount of whisker-forming material added is reported in Table 1 in % by weight based on the total weight of HAP plus whisker-forming material.

Anorthite: a mixture of $SiO_2$ 61% by weight, $Al_2O_3$ 17% by weight, and CaO 22% by weight Diopside: a mixture of $SiO_2$ 61% by weight, MgO 12% by weight, and CaO 27% by weight The dispersant was SN Dispersant 5045 manufactured and sold by SAN NAPCO Limited and was used in an amount of 0.05% by weight based on the total weight of HAP plus whisker forming material.

The thus obtained ceramic materials which contained whiskers were measured for grain boundary vitreous phase thickness, relative density, flexural strength, and toughness ($K_{IC}$). The results are shown in Table 2.

Comparative samples outside the scope of the invention are also reported in Tables 1 and 2. All the samples within the scope of the invention were observed to have an intermediate layer along the entire grain-whisker boundary, but comparative sample No. 13 showed less desirable properties because of partial presence of an intermediate layer.

For ceramic material sample No. 4 (HAP-diopside), a change of composition across its intermediate layer was analyzed using a photomicrograph under a TEM. The results are shown in FIG. 1. It is seen that the grain boundary vitreous phase contains Ca, P and Si in continuous linear gradient concentrations and that the gradient of the concentration of Si is opposite to those of Ca and P.

EXAMPLE 2

Figure 2:
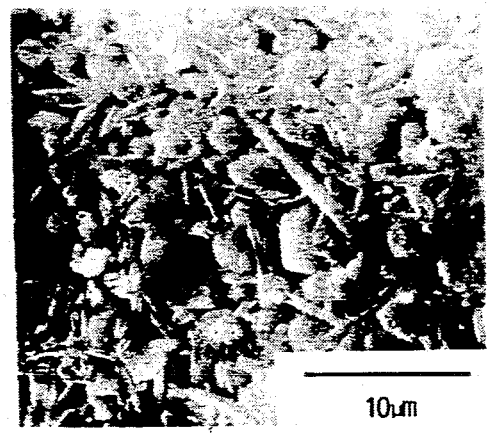
FIG. 2 is a SEM photomicrograph of the ceramic material of Example 2.
Figure 3:
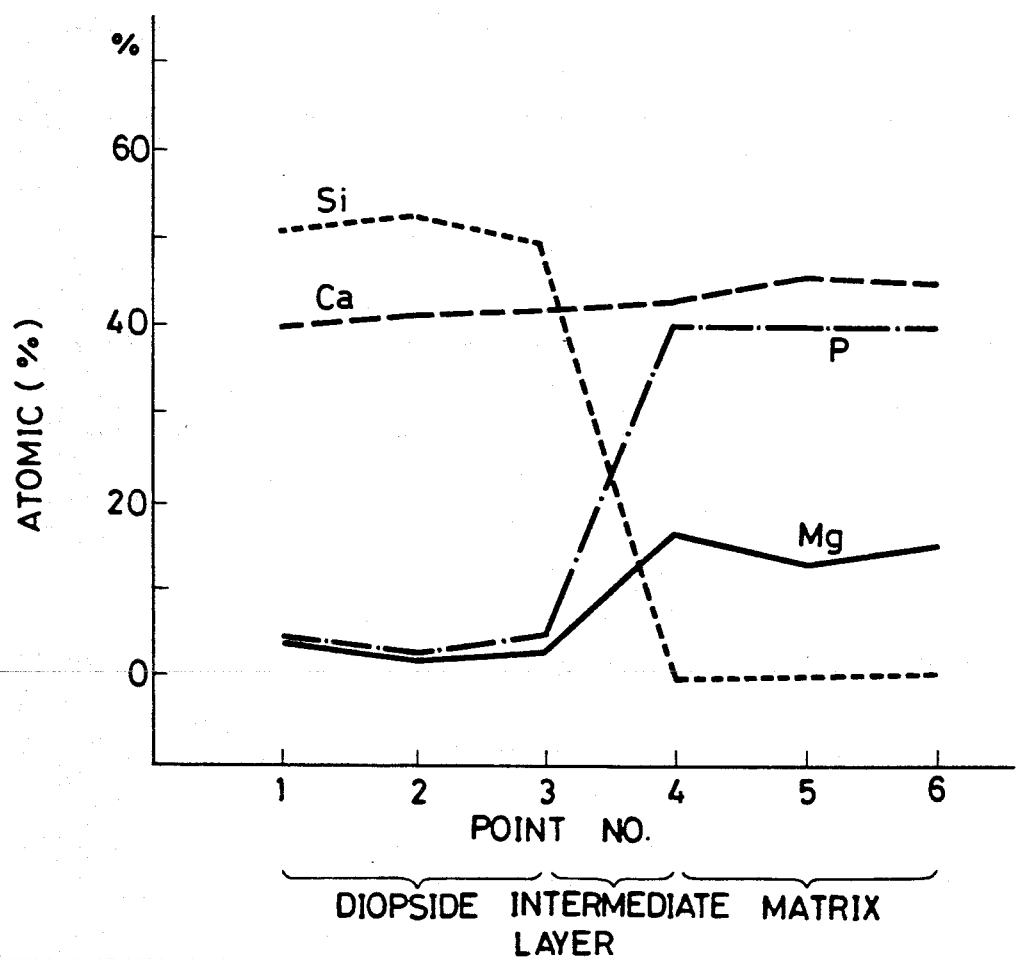
FIG. 3 is a diagram showing a change of the composition across an intermediate layer in the ceramic material of Example 2.
Figure 4:
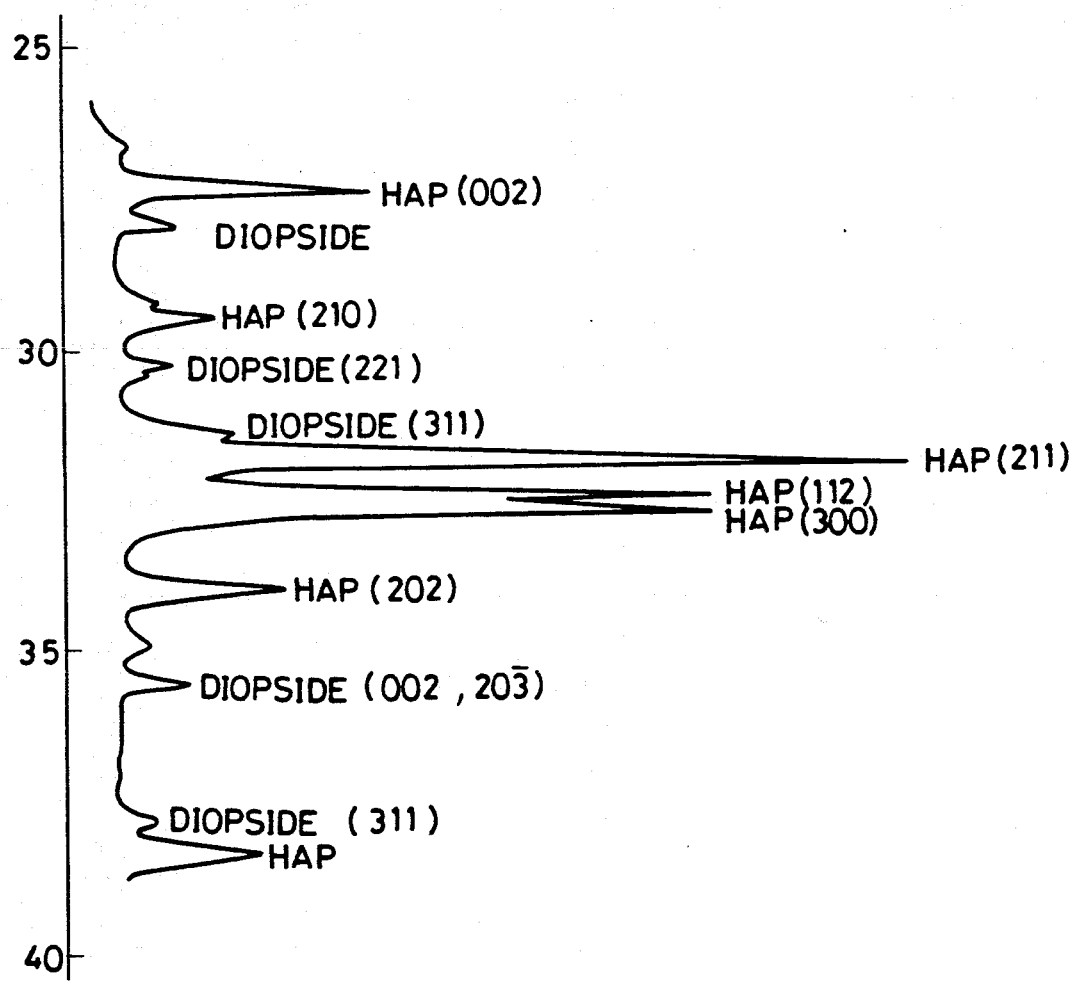
FIG. 4 is a diagram of X-ray diffraction analysis of the ceramic material of Example 2.

To a matrix-forming HAP having a Ca/P atom ratio of 1.67 and a BET value of 65 $m^2/g$ was added 20% by weight of a diopside powder having the composition: $SiO_2$ 62.5%, CaO 23.3%, and MgO 14.27% by weight (stoichiometric composition: $SiO_2$ 55.5%, CaO 25.9%, and MgO 18.6%). The mixture was heated in air at 1230° C. for 2 hours and then slowly cooled down. FIG. 2 shows the microstructure of this composite sintered body (HAP-diopside) under an SEM. The ceramic material had a matrix grain size of 2 to 4 μm, a whisker length of 4 to 8 μm. and a whisker aspect ratio of 10 to 15. FIG. 3 shows the result of a TEM examination of the grain boundary. There was formed an intermediate layer of CaO. $SiO_2$-$P_2O_5$-MgO system at the grain boundary. It was found that part of the HAP changed into tricalcium phosphate including Mg, and part of the diopside changed into wollastonite as a result of interaction between HAP and diopside. FIG. 4 is an X-ray diffraction diagram of this composite sintered body (HAP-diopside).

Table 3 shows several mechanical properties of the ceramic material (HAP-diopside) and the HAP itself, including bending strength ($\sigma_f$), Young's modulus (E), fracture toughness ($K_{IC}$), Poisson's ratio ($\nu$), density, critical flaw size (c), and dimensionless crack geometry constant ($\gamma$).

TABLE 1

| Sample No. | HAP BET ($m^2/g$) | Whiskers Type | Composition | Amount (wt %) | Sintering temp. (°C.) | Cooling rate (°C./min.) |
|---|---|---|---|---|---|---|
| 1 | 80 | Diopside | $SiO_2$.CaO.MgO | 20 | 1220 | 1 |
| 2 | 80 | Diopside | $SiO_2$.CaO.MgO | 20 | 1220 | 5 |
| 3 | 80 | Diopside | $SiO_2$.CaO.MgO | 20 | 1220 | 10 |
| 4 | 80 | Diopside | $SiO_2$.CaO.MgO | 20 | 1220 | 20 |
| 5 | 80 | Diopside | $SiO_2$.CaO.MgO | 60 | 1220 | 20 |
| 6 | 10 | Anorthite | $SiO_2$.$Al_2O_3$.CaO | 20 | 1280 | 1 |
| 7 | 10 | Anorthite | $SiO_2$.$Al_2O_3$.CaO | 20 | 1280 | 5 |
| 8 | 10 | Anorthite | $SiO_2$.$Al_2O_3$.CaO | 20 | 1280 | 10 |
| 9 | 10 | Anorthite | $SiO_2$.$Al_2O_3$.CaO | 20 | 1280 | 20 |
| 11* | 80 | Diopside | $SiO_2$.CaO.MgO | 20 | 1220 | 40 |
| 12* | 80 | Diopside | $SiO_2$.CaO.MgO | 20 | 1220 | 60 |
| 13* | 10 | Anorthite | $SiO_2$.$Al_2O_3$.CaO | 20 | 1280 | 40 |
| 14* | 10 | Anorthite | $SiO_2$.$Al_2O_3$.CaO | 20 | 1280 | 60 |
| 15* | 80 | Diopside | $SiO_2$.CaO.MgO | 20 | 1220 | 0.1 |
| 16* | 80 | Anorthite | $SiO_2$.$Al_2O_3$.CaO | 20 | 1280 | 0.1 |

*outside the scope of the invention

TABLE 2

| Sample No. | Whisker content (area %) | Intermediate layer thickness (μm) | Relative density (%) | Flexural strength (MPa) | Toughness (MPa $\sqrt{m}$) |
|---|---|---|---|---|---|
| 1 | 15 | 0.05 | 99.5 | 230 | 3.0 |
| 2 | 15 | 0.05 | 99.6 | 230 | 3.0 |
| 3 | 18 | 0.07 | 99.5 | 240 | 3.5 |
| 4 | 18 | 0.07 | 99.7 | 300 | 3.5 |
| 5 | 50 | 0.07 | 99.3 | 380 | 4.5 |
| 6 | 8 | 0.08 | 99.7 | 180 | 2.5 |
| 7 | 10 | 0.07 | 99.0 | 180 | 2.5 |
| 8 | 10 | 0.08 | 99.3 | 190 | 2.7 |
| 9 | 15 | 0.09 | 99.5 | 190 | 2.7 |
| 11* | 10 | none | 99.0 | 180 | 1.3 |
| 12* | 12 | none | 99.3 | 180 | 1.2 |
| 13 | 8 | partial, 0.05 | 99.0 | 170 | 1.5 |
| 14* | 8 | none | 99.0 | 160 | 1.2 |
| 15* | 13 | 5.0 | 99.5 | 180 | 1.5 |
| 16* | 10 | 4.0 | 99.5 | 160 | 1.0 |

*outside the scope of the invention

TABLE 3

| | Mechanical properties | | | | | |
|---|---|---|---|---|---|---|
| | $\sigma_f$ (MPa) | E (GPa) | $K_{IC}$ (MPam) | $\nu$ | Density (g/cm$^2$) | c ($\mu$m) | $\gamma$ (J/m$^2$) |
| HAP | 103 | 47 | 1.2 | 0.26 | 3.16 | 22 | 14 |
| HAP-diopside | 300 | 83 | 3.2 | 0.21 | 3.13 | 30 | 59 |

It was found that the bending strength and fracture toughness of the composite HAP-diopside sintered body were 2 or 3 times those of the HAP.

EXAMPLE 3

To a hydroxyapatite (HAP) powder having a specific surface area (BET) of 80 m$^2$/g were added pre-formed whiskers whose type and amount are shown in Table 4 and if desired, 2% by weight of the intermediate layer-forming material shown in Table 4. The mixture was milled and molded under the same conditions as in Example 1. The molded material was sintered at a temperature of 1200° C. for 2 hours, and then slowly cooled down at a rate of 20° C./min., obtaining a ceramic material.

The ceramic materials had a matrix grain size of 2 $\mu$m, a whisker length of 3 $\mu$m, and a whisker aspect ratio of 15. The intermediate layer therein had the thickness shown in Table 4. The relative density, flexural strength, and toughness of these ceramic materials are also shown in Table 4.

COMPARATIVE EXAMPLE 1

The procedure of Example 3 was repeated except that the cooling rate was increased to 50° C./min. There was obtained a ceramic material which had a matrix grain size of 2 pm, a whisker length of 3 $\mu$m, and a whisker aspect ratio of 15. No intermediate layer was observed. The relative density, flexural strength, and toughness of this ceramic material are shown in Table 5.

The procedure of Comparative Example 1 was repeated except that the diopside whiskers were replaced by the whiskers shown in Table 5. The mechanical properties of the resulting ceramic materials are also shown in Table 5.

TABLE 5

| Sample No. | Whisker material | Intermediate layer thickness | Relative density (%) | Flexural strength (MPa) | Toughness (MPa $\sqrt{m}$) |
|---|---|---|---|---|---|
| 41* | Diopside CaO.2SiO$_2$.MgO | — | 99.5 | 130 | 1.2 |
| 42* | Wollastonite CaO.2SiO$_2$ | — | 99.5 | 130 | 1.0 |
| 43* | Mullite 3Al$_2$O$_3$.2SiO$_2$ | — | 99.5 | 130 | 1.0 |
| 44* | 3CaO.SiO$_2$ | — | 99.5 | 120 | 1.0 |
| 45* | Alumina | — | 99.5 | 110 | 0.9 |
| 46* | Zirconia | — | 99.5 | 120 | 0.8 |
| 47* | SiC | — | 99.5 | 110 | 0.7 |
| 48* | SiN | — | 99.5 | 100 | 0.7 |
| 49* | Carbon | — | 99.5 | 100 | 0.7 |
| 50* | Titanium | — | 99.5 | 100 | 0.7 |

*outside the scope of the invention

As seen from the data of Examples and Comparative Examples, the ceramic materials of the invention are improved in mechanical strength, especially toughness over the comparative samples.

TABLE 4

| Sample No. | Whisker Material | Content (area %) | Intermediate layer Forming material | Thickness ($\mu$m) | Relative density (%) | Flexural strength (MPa) | Toughness (MPa $\sqrt{m}$) |
|---|---|---|---|---|---|---|---|
| 21 | Diopside CaO$_2$.2SiO$_2$.MgO | 18 | — | 0.07 | 99.5 | 180 | 2.4 |
| 22 | Diopside CaO$_2$.2SiO$_2$.MgO | 54 | — | 0.07 | 99.5 | 360 | 4.3 |
| 23 | Anorthite CaO.2SiO$_2$.Al$_2$O$_3$ | 20 | — | 0.07 | 99.5 | 180 | 2.3 |
| 24 | Anorthite CaO.2SiO$_2$.Al$_2$O$_3$ | 60 | — | 0.07 | 99.5 | 350 | 4.3 |
| 25 | Wollastonite CaO.SiO$_2$ | 21 | — | 0.05 | 99.8 | 180 | 2.2 |
| 26 | Mullite 3Al$_2$O$_3$.2SiO$_2$ | 22 | — | 0.10 | 99.7 | 170 | 2.1 |
| 27 | 3CaO.Al$_2$O$_3$ | 23 | — | 0.10 | 99.6 | 170 | 2.0 |
| 28 | Alumina | 20 | CaCO$_3$ | 0.10 | 99.5 | 180 | 2.0 |
| 29 | Zirconia | 21 | CaCO$_3$ | 0.10 | 99.5 | 180 | 1.8 |
| 30 | SiC | 20 | SiO$_2$ | 0.08 | 99.4 | 180 | 1.9 |
| 31 | SiN | 20 | SiO$_2$ | 0.05 | 99.3 | 170 | 1.8 |
| 32 | Carbon | 20 | CaCO$_3$ | 0.05 | 99.5 | 180 | 1.8 |
| 33 | Titanium | 20 | CaCO$_3$ | 0.05 | 99.5 | 180 | 1.8 |

EXAMPLE 4

The ceramic materials prepared in Example 3 were shaped into rectangular implants of 3×4×5 mm which were implanted in the lower edge of the jaw bone of adult rabbits. Polished, but non-decalcified specimens were prepared from the implanted jaw bones after 2 and 4 weeks from the implanting operation. A SEM photomicrograph was taken on the interface between the implant and the newly grown bone. Evaluation was made in terms of % by area of bond in the SEM photomicrograph according to the following ratings.

Excellent: 20% or more of the implant directly bonded to the bone
Good: less than 20% of the implant directly bonded to the bone
Poor: no bond to the bone The results are shown in Table 6.

TABLE 6

| Sample No. | After 2 weeks | After 4 weeks |
|---|---|---|
| 21 | Excellent | Excellent |
| 23 | Excellent | Excellent |
| 26 | Good | Excellent |
| 28 | Poor | Excellent |
| 30 | Poor | Excellent |
| 33 | Poor | Good |

As is evident from Table 6, the ceramic materials falling within the scope of the invention have improved biological affinity.

Although some preferred embodiments have been described, many modifications and variations may be made thereto in the light of the above teachings. It is therefore to be understood that within the scope of the appended claims, the invention may be practiced otherwise than as specifically described.

We claim:

1. A ceramic material in the form of a composite sintered body comprising crystalline calcium phosphate grains as a matrix and inorganic whiskers dispersed therein wherein an intermediate layer having a thickness of from 0.005 to 3 microns and containing at least one element present in either one or both of the whiskers and the grains intervenes between the whiskers and the grains.

2. The ceramic material of claim 1 wherein said intermediate layer has a continuous or stepwise gradient of concentration.

3. The ceramic material of claim 2 wherein in said intermediate layer, the gradient of concentration of elements in the whiskers is opposite to the gradient of concentration of elements in the grains.

4. The ceramic material of claim 1 wherein the crystalline calcium phosphate is an apatite.

5. The ceramic material of claim 4 wherein the crystalline calcium phosphate is a hydroxyapatite having an atomic calcium-to-phosphorus (Ca/P) ratio of from 165/100 to 175/100.

6. The ceramic material of claim 1 wherein the inorganic whiskers are selected from the group consisting of silicon carbide, boron carbide, silicon nitride, carbon, alumina, zirconia, calcium silicate, aluminum silicate, aluminum silicate calcium, calcium silicate magnesium, calcium aluminate, magnesium silicate, and metal whiskers.

7. The ceramic material of claim 1 or 6 wherein the inorganic whiskers contains at least one inorganic oxide selected from the group consisting of calcium oxide, silicon oxide, aluminum oxide, and magnesium oxide.

8. The ceramic material of claim 1 wherein the whiskers occupy 0.5 to 95% by area of a cross section of the sintered body.

9. The ceramic material of claim 1 wherein the matrix has a grain size of 0.05 to 30 μm, and the whiskers have a length of 0.05 to 2,000 μm and an aspect ratio as defined by length/diameter of from 1.2/1 to 100/1, the ratio of matrix grain size to whisker length ranging from 10/1 to 1/10.

10. A method for preparing a ceramic material in the form of a composite sintered body comprising crystalline calcium phosphate grains as a matrix and inorganic whiskers dispersed therein wherein an intermediate layer containing at least one element contained in either one or both of the whiskers and the grains intervenes between the whiskers and the grains, comprising
   mixing a calcium phosphate material and about 0.5 to 95% by weight of an inorganic whisker-forming material based on the total weight of the calcium phosphate material and the inorganic whisker-forming material,
   sintering the mixture at a temperature of 800 to 1600° C. for a sufficient time to tallow whiskers to grow, and
   cooling the mixture from the sintering temperature at a rate of 0.1 to 30° C./min to allow said intermediate layer to form between the matrix grains and the whiskers.

11. A method for preparing a ceramic material in the form of a composite sintered body comprising crystalline calcium phosphate grains as a matrix and inorganic whiskers dispersed therein wherein an intermediate layer containing at least one element contained in either one or both of the whiskers and the grains intervenes between the whiskers and the grains, comprising
   mixing a calcium phosphate material and about 0.5 to 95% by weight of inorganic whiskers based on the total weight of the calcium phosphate material and the inorganic whiskers,
   sintering the mixture at a temperature of 800 to 1600° C., and
   cooling the mixture from the sintering temperature at a rate of 0.1 to 30° C./min to allow said intermediate layer to form between the matrix grains and the whiskers.

12. A method for preparing a ceramic material in the form of a composite sintered body comprising crystalline calcium phosphate grains as a matrix and inorganic whiskers dispersed therein wherein an intermediate layer containing at least one element contained in either one or both of the whiskers and the grains intervenes between the whiskers and the grains, comprising
   mixing a calcium phosphate material, about 0.5 to 95% by weight of inorganic whiskers based on the total weight of the calcium phosphate material, inorganic whiskers and intermediate layer-forming material, and about 0.05 to about 5% by weight of an intermediate layer-forming material based on said total weight,
   sintering the mixture at a temperature of 800 to 1600° C., and
   cooling the mixture from the sintering temperature at a rate of 0.1 to 30° C./min to allow said intermediate layer to form between the matrix grains and the whiskers.

13. The ceramic material of claim 1, wherein said intermediate layer has a thickness of from 0.01 to 1.0 microns.

14. The method of claim 10, wherein the cooling step, the cooling rate is in the range of from 0.5 to 10° C./min.

15. The method of claim 11, wherein the cooling step, the cooling rate is in the range of from 0.5 to 10° C./min.

16. The method of claim 12, wherein the cooling step, the cooling rate is in the range of from 0.5 to 10° C./min.

* * * * *

UNITED STATES PATENT AND TRADEMARK OFFICE
CERTIFICATE OF CORRECTION

PATENT NO. : 5,082,808
DATED : January 21, 1992
INVENTOR(S) : Tohru Nonami et al.

It is certified that error appears in the above-identified patent and that said Letters Patent is hereby corrected as shown below:

Title page, item (63):

The Related U.S. Application Data is incorrect, should be,

--Continuation of Ser. No. 441,775, Nov. 27, 1989, abandoned, which is a CIP of Ser. No. 374,989, Jul. 3, 1989.--.

Signed and Sealed this

Fifteenth Day of June, 1993

Attest:

MICHAEL K. KIRK

*Attesting Officer*     Acting Commissioner of Patents and Trademarks

UNITED STATES PATENT AND TRADEMARK OFFICE
CERTIFICATE OF CORRECTION

PATENT NO. : 5,082,808
DATED : JANUARY 21, 1992
INVENTOR(S) : TOHRU NONAMI ET AL

It is certified that error appears in the above-identified patent and that said Letters Patent is hereby corrected as shown below:

Column 14, Claim 11, line 40, before "95%", insert --about--.

Column 14, Claim 12, line 57, before "95%", insert --about--.

Signed and Sealed this

Twentieth Day of July, 1993

Attest:

MICHAEL K. KIRK

Attesting Officer     Acting Commissioner of Patents and Trademarks